United States Patent [19]
Loiacono

[11] 3,970,090
[45] July 20, 1976

[54] CATHETER

[75] Inventor: Vincent R. Loiacono, New London, Conn.

[73] Assignee: Physio Medics, Inc., New London, Conn.

[22] Filed: Feb. 3, 1975

[21] Appl. No.: 546,393

[52] U.S. Cl. ............................ 128/349 R; 128/245
[51] Int. Cl.² ...................................... A61M 25/00
[58] Field of Search .................... 128/239, 241–245, 128/343, 348–351, 2 A, 151, 152

[56] References Cited
UNITED STATES PATENTS

| | | | |
|---|---|---|---|
| 3,123,069 | 3/1964 | Laisne et al. | 128/152 |
| 3,344,791 | 10/1967 | Foderick | 128/349 R |
| 3,482,576 | 12/1969 | Ericson et al. | 128/349 BV |
| 3,583,404 | 6/1971 | McWhorter | 128/349 BV |
| 3,721,229 | 3/1973 | Panzer | 128/348 X |
| 3,810,474 | 5/1974 | Cross | 128/349 B X |

FOREIGN PATENTS OR APPLICATIONS

| 325,740 | 1/1903 | France | 128/349 B |
|---|---|---|---|

*Primary Examiner*—Dalton L. Truluck
*Attorney, Agent, or Firm*—McCormick, Paulding & Huber

[57] ABSTRACT

A catheter having a body made from elastomeric material and including a tubular inner part defining a fluid passageway having an inlet end and an outlet end. A tubular outer retention sleeve integrally connected only at the inlet end to the inner part extends in the direction of the outlet end in axially surrounding relation to the inner part. The retention sleeve is biased to a normal retention configuration for engaging the peripheral wall of an associated body passageway to releasably retain the catheter in preselected position therein and is stretchable to an insertion configuration to permit the catheter to be freely inserted into the body passageway and removed therefrom. A valve provides a closure for the outlet end. A frangible wall portion of the inner part between the inlet opening and the valve is constructed and arranged to rupture in response to predetermined fluid pressure within the passageway to vent fluid therefrom.

10 Claims, 7 Drawing Figures

U.S. Patent  July 20, 1976  3,970,090
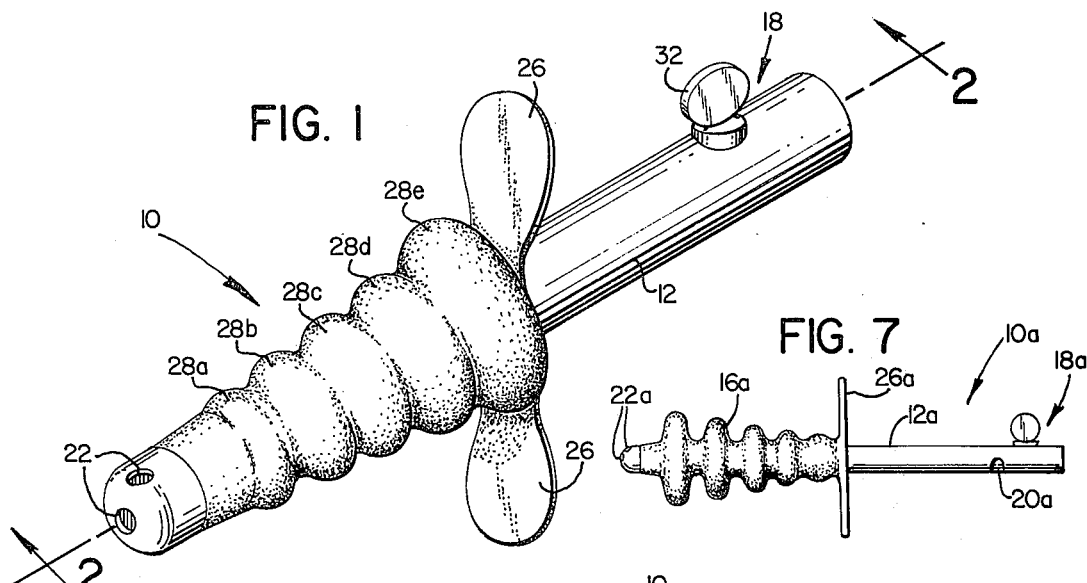
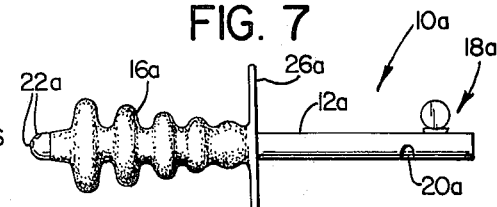
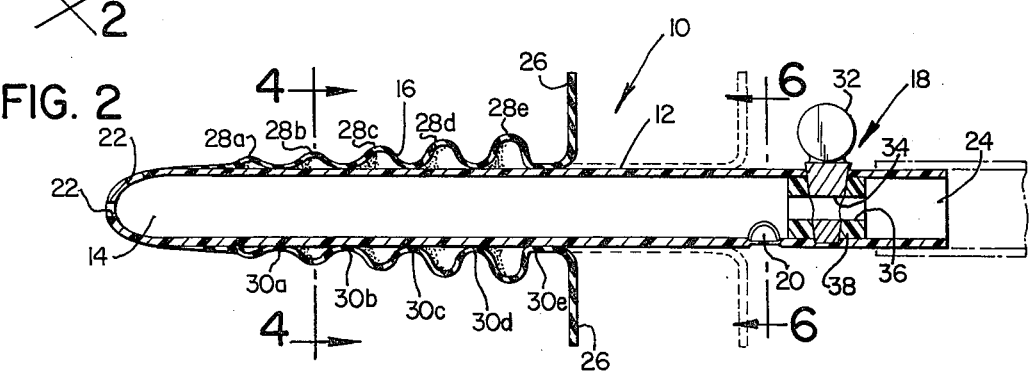
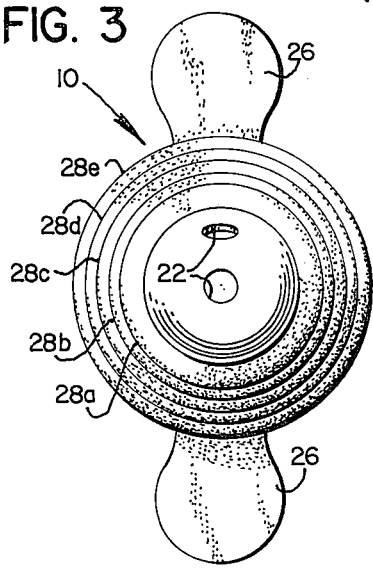
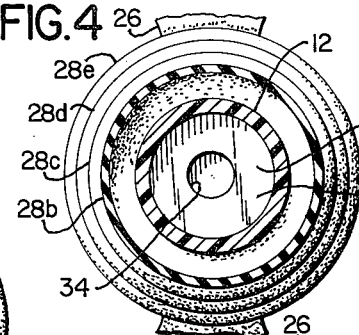
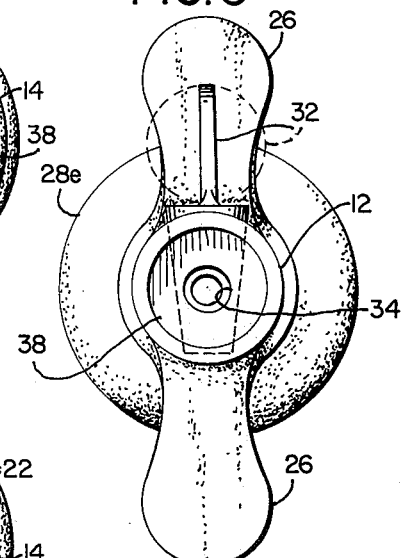
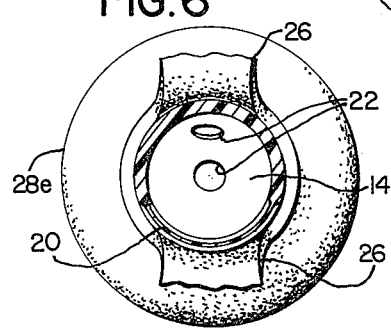

CATHETER

BACKGROUND OF THE INVENTION

This invention relates in general to catheters and deals more particularly with a catheter which includes valve means for controlling fluid flow from an associated body passageway. The catheter of the present invention may be used to control fluid discharge from any associated body passageway, however, the present catheter is particularly suitable for use as a urethral catheter. The present catheter is provided to fill the general need for an improved catheter which may be applied without surgical technique and which may, in some instances be applied by the patient himself. The present catheter is particularly suitable for use by a convalescing patient to enable fluid control not attainable by normal physiological means.

SUMMARY OF THE INVENTION

In accordance with the present invention an improved catheter is provided which includes a tubular inner part defining a fluid passageway having a fluid inlet opening at one end and a fluid outlet opening at the other end thereof. An axially elongated elastomeric tubular outer retention sleeve integrally connected to the inlet end of the inner part extends in concentric surrounding relation thereto and in the direction of the outlet end. The sleeve has a normal retention configuration and is deformable to an insertion configuration. Valve means is provided for closing the outlet end of the passageway. Pressure relief means associated with the tubular inner part and disposed between the inlet end and the valve means vents fluid from the passageway in response to a predetermined fluid condition therein.

BRIEF DESCRIPTION OF THE DRAWING

FIG. 1 is a perspective view of a catheter embodying the present invention.

FIG. 2 is a sectional view taken generally along the line 2—2 of FIG. 1.

FIG. 3 is a somewhat enlarged inlet end elevational view of the catheter of FIG. 1.

FIG. 4 is a somewhat enlarged fragmentary sectional view taken along the line 4—4 of FIG. 2.

FIG. 5 is a somewhat enlarged outlet end elevational view of the catheter of FIG. 1.

FIG. 6 is a somewhat enlarged fragmentary sectional view taken along the line 6—6 of FIG. 2.

FIG. 7 is a side elevational view of another catheter embodying the present invention.

DETAILED DESCRIPTION OF THE PREFERRED EMBODIMENT

The catheter of the present invention is constructed and arranged for insertion into and retention in a body passageway or cavity to control fluid flow therefrom. Turning now to the drawing, a catheter embodying the present invention and indicated generally by the reference numeral 10 is particularly adapted to function as a urethral catheter to control urine flow from the bladder. The catheter 10 has a body, preferably made from resilient, elastomeric material, such as rubber or plastic, and which comprises an axially elongated tubular inner part 12 which defines a fluid passageway 14 and an outer tubular retention sleeve 16 which is connected to the inner part 12 at the inlet end of the body and which extends in the direction of the body outlet end in concentric surrounding relation with the tubular inner part. The retention sleeve 16 has a normal retention configuration for engaging the peripheral wall of an associated body passageway, as for example, a urethral passageway (not shown) to releasably retain the catheter 10 in a preselected position within the body passageway. The retention sleeve 16 is deformable to an insertion configuration to permit the catheter 10 to be freely inserted into the body passageway or cavity, as will be hereinafter further discussed. A valve, indicated generally at 18, is provided for selectively closing the outlet end of the passageway 14 to prevent fluid flow therefrom. The illustrated catheter 10 also includes pressure relief means indicated at 20 for venting fluid from fluid passageway 14 in response to a predetermined fluid pressure condition therein.

Considering now the catheter 10 in further detail, the body of the catheter is preferably made from soft rubber or the like and has a rounded, blunt inlet end which has a plurality of inlet openings 22, 22 therethrough communicating with the fluid passageway 14. The inner part 12 comprises a generally cylindrical tubular part which has an outlet opening 24 at its outlet end. The retention sleeve 16 comprises a substantially imperforate tubular sleeve integrally connected to the inner part 12 at only the inlet end of the catheter body. The sleeve 16 is preferably generally conical and extends in the direction of the outlet end in concentric surrounding relation to the inner part. At its free end the retention sleeve has a pair of diametrically opposed ears or tabs 26, 26 which project radially outwardly therefrom to provide a means for gripping the sleeve to move it relative to the inner part 12. The sleeve 16 is inherently biased to a retention configuration shown in FIG. 1 and in full lines in FIG. 2 and is stretchable in the direction of the outlet end of the body to an insertion configuration generally indicated by broken lines in FIG. 2. In its normal retention condition, the sleeve 16 is characterized by an undulated outer peripheral surface defined by an axial series of annular portions including alternately arranged radially enlarged portions 28a-28e and radially reduced portions 30a-30e. The radially reduced portions 30a-30e are arranged for general annular engagement with associated portions of the peripheral surface of said tubular inner part 12, as shown in FIG. 2. The conical retention sleeve 16 in its retention condition diverges toward the outlet end of the inner part 12 and is stretchable to its insertion configuration to effect generally radially contraction of said radially enlarged annular portions 28a-28e substantially as shown in FIG. 2

Various valve arrangements may be employed to provide a closure for the outlet end of the catheter body. However, in the presently preferred catheter the valve comprises an integral part of the catheter and includes a valve element which is at least partially disposed within the fluid passageway 14 to provide a closure within the passageway. More specifically, the illustrated valve 18 comprises a stopcock which includes a rotary valve element 32 arranged with its axis generally normal to the axis of the tubular part 12 for angular movement between open and closed positions. The valve element 32 has a cylindrical passageway 34 therethrough which is coaxially aligned with another cylindrical passageway 36 formed in a plug 38 disposed within passageway 14. The passageways 34 and 36 communicate with the passageway 14 to provide a flow path to the outlet opening 24 when the valve element 32 is in its open position, as it appears in full lines in FIGS. 1, 2 and 5. Rotation of the valve element 32 about its axis and through an angle of approximately 90° and to its broken line position in FIGS. 2 and 5, closes the valve or stopcock 18.

As previously noted, means is provided for venting fluid from the passageway 14 in response to a predetermined pressure condition therein. The pressure relief means is associated with the body of the catheter and located between the inlet end of the catheter body and the valve means thereof. In the illustrated embodiment 10, the pressure relief means 20 comprises a frangible wall portion of the tubular inner part 12. The latter wall portion is constructed and arranged to rupture in response to occurrence of a predetermined fluid pressure condition within the passageway 14 to provide an alternate fluid outlet path from the passageway 14 when the valve 18 is closed.

To insert the catheter 10 in a body passageway, the tabs 26, 26 are gripped and the retention sleeve 16 is stretched relative to the inner part 12 and in the direction of the outlet end. The inner part has sufficient structural integrity to resist deformation when the retention sleeve is stretched to its insertion position, as indicated in broken lines in FIG. 2. The sleeve 16 is maintained in the latter position until the catheter is inserted to a predetermined position within the body passageway. The tabs 26, 26 are then released to permit the retention sleeve 16 to return to its normal retention position wherein the annular enlarged portions 28a-28e grip the inner peripheral wall of the body passageway to retain the catheter therein. The catheter 10 may be removed from the body passageway by stretching the retention sleeve 16 to its insertion position, generally as aforedescribed.

Referring now to FIG. 7 another urethral catheter embodying the present invention and having improved retention characteristics is indicated generally by the reference numeral 10a. The catheter 10a is similar in most respects to the catheter 10 previously described and differs therefrom only in the construction and arrangement of its retention sleeve 16a. More specifically, the sleeve 16a in its normal retention condition, as it appears in FIG. 7, is larger at its inlet end than at its outlet end and has a generally undulated peripheral surface which converges from the inlet toward the outlet end of the catheter. This arrangement provides for tight gripping engagement between the retention sleeve 16a and the inner surface of an associated body passageway in the vicinity of the catheter inlet end and may be particularly desirable for some usages. However, it should be understood that the retention sleeve need not have a conical configuration. Thus, the catheter may also be made with a generally cylindrical retention sleeve which preferably has a slight undulated configuration in its retention condition and such forms of the catheter are also contemplated within the scope of the present invention.

I claim:

1. A catheter comprising an axially elongated tubular inner part defining a single fluid drainage passageway having a fluid inlet opening at one end and a fluid outlet opening at the other end thereof, an axially elongated elastomeric outer tubular retention sleeve integrally connected to said tubular inner part at only said one end and extending in the direction of said other end in concentric surrounding relation to said tubular inner part, said retention sleeve having a normal retention configuration characterized by an undulated outer peripheral surface defined by an axial series of annular portions including alternately arranged radially enlarged annular portions and radially reduced annular portions for engaging the peripheral wall of an associated body passageway to releasably retain said catheter in preselected position within the body passageway, said radially reduced portions of said retention sleeve being in general annular engagement with the peripheral surface of said tubular inner part when said sleeve is in its retention configuration, said retention sleeve being stretchable in the direction of said other end to an insertion configuration to permit said catheter to be freely inserted into the body passageway and removed therefrom, said retention means having gripping means at its free end providing surfaces for manual gripping to stretch the retention sleeve axially of said inner tubular part and to its insertion configuration, valve means for closing the outlet end of said passageway to prevent passage of fluid therethrough, and fluid pressure relief means associated with said tubular inner part and disposed between said inlet end and said valve means for venting fluid from said fluid drainage passageway in response to a predetermined fluid pressure condition therein.

2. A catheter as set forth in claim 1 wherein said pressure relief means comprises a frangible portion of said tubular inner part for rupture in response to the occurance of said predetermined fluid pressure within said fluid passageway.

3. A catheter as set forth in claim 2 wherein said frangible portion comprises a weakened portion of the wall of said tubular inner part.

4. A catheter as set forth in claim 1 wherein said valve means comprises a valve element partially disposed within said fluid passageway for providing a closure within said passageway.

5. A catheter as set forth in claim 4 wherein said valve element comprises a stopcock.

6. A catheter as set forth in claim 1 wherein said gripping means comprises a generally radially disposed tab integrally connected to said retention sleeve.

7. A catheter as set forth in claim 1 wherein said sleeve in its normal retention condition is further characterized by a generally conical configuration.

8. A catheter as set forth in claim 7 wherein said sleeve in its normal retention condition converges from said one end toward said other end.

9. A catheter as set forth in claim 7 wherein said sleeve in its normal retention condition diverges from said one end toward said other end.

10. A catheter comprising an axially elongated generally cylindrical tubular inner part defining a single fluid passageway and having a fluid inlet opening at one end and a fluid outlet opening at the other end thereof, an axially elongated elastomeric outer tubular retention sleeve of substantially uniform thickness integrally connected to said inner part at only said one end and extending in the direction of said other end in generally concentric surrounding relation with an associated portion of said inner part, said retention sleeve being substantially imperforate and having a normal retention configuration characterized by an undulated outer peripheral surface defined by an axially spaced series of alternately arranged radially enlarged annular portions and radially reduced annular portions for engaging the peripheral wall of an associated body passageway to releasably retain said catheter in preselected position with the body passageway, said radially reduced portions of said sleeve being in general annular engagement with the peripheral surface of said tubular inner part, said retention sleeve being stretchable in one axial direction and toward said other end to an insertion configuration for effecting radial contraction of said enlarged annular portions to permit said catheter to be freely inserted into the body passageway, said retention sleeve having a pair of diametrically opposed tabs at its free end projecting generally radially outwardly therefrom to provide means for gripping the retention sleeve to move it relative to said tubular inner part, valve means associated with said inner part and partially disposed within said fluid passageway and movable within said fluid passageway and relative thereto for closing said fluid passageway for closing the outlet end of said fluid passageway, and fluid pressure relief means comprising a frangible portion of said inner part for rupture in response to a predetermined fluid pressure within said fluid passageway to vent fluid from said fluid passageway.

* * * * *

UNITED STATES PATENT OFFICE
CERTIFICATE OF CORRECTION

PATENT NO. : 3,974,090
DATED : August 10, 1976
INVENTOR(S) : Robert S. Mitchell

It is certified that error appears in the above-identified patent and that said Letters Patent are hereby corrected as shown below:

Column 4, line 32 " salt, such as its mono- or diammonium salts, and mono-" should read --- salts, such as its mono- or diammonium salts, and mono- ---.

Column 5, line 55, "While it is not essentially that water must be present" should read --- While it is not essential that water must be present ---.

Column 16, Claim 30, line 8, after "ammonium ions" should appear --- , alkylammonium ions ---.

Signed and Sealed this

Twenty-third Day of November 1976

[SEAL]

Attest:

RUTH C. MASON
Attesting Officer

C. MARSHALL DANN
Commissioner of Patents and Trademarks